United States Patent
Tojo et al.

(10) Patent No.: US 10,047,068 B2
(45) Date of Patent: Aug. 14, 2018

(54) OPTICAL RESOLUTION METHOD OF LENALIDOMIDE

(71) Applicant: Shiseido Company, Ltd, Chuo-ku, Tokyo (JP)

(72) Inventors: Yosuke Tojo, Yokohama (JP); Masashi Mita, Tokyo (JP); Wolfgang Lindner, Klosterneuburg (AT)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 15/312,788

(22) PCT Filed: May 21, 2015

(86) PCT No.: PCT/JP2015/064643
§ 371 (c)(1),
(2) Date: Nov. 21, 2016

(87) PCT Pub. No.: WO2015/178461
PCT Pub. Date: Nov. 26, 2015

(65) Prior Publication Data
US 2017/0190686 A1    Jul. 6, 2017

(30) Foreign Application Priority Data
May 22, 2014    (JP) ................... 2014-106388

(51) Int. Cl.
*C07D 401/04*    (2006.01)

(52) U.S. Cl.
CPC ................. *C07D 401/04* (2013.01)

(58) Field of Classification Search
CPC .................................................... C07D 401/04
USPC .......................................................... 546/201
See application file for complete search history.

(56) References Cited

FOREIGN PATENT DOCUMENTS

| WO | WO 02/064083 A2 | 8/2002 |
|---|---|---|
| WO | WO 03/097052 A2 | 11/2003 |
| WO | WO 2010/056344 A1 | 5/2010 |
| WO | WO 2011/069608 A1 | 6/2011 |

OTHER PUBLICATIONS

Saravanan et al., "Development of, etc.," Chromatographia 2007, 66, (3/4), 287-290.*
Walz et al., "Investigation of the enantiomerization barriers of the phthalimidone derivatives EM12 and lenalidomide by dynamic electrokinetic chromatography," Electrophoresis, 2015, 36(5):796-804.

* cited by examiner

*Primary Examiner* — Patricia L Morris
(74) *Attorney, Agent, or Firm* — Foley & Lardner LLP

(57) ABSTRACT

The problem addressed by the present invention is to provide a novel method for separating and purifying pure enantiomer of lenalidomide. Pure enantiomer of lenalidomide can be separated and purified by using, as the mobile phase, an organic solvent selected from the group consisting of aprotic solvents, secondary alcohols, and mixtures thereof.

7 Claims, 12 Drawing Sheets

*Total amount of LL injected was 180 mg as racemic form.

OPTICAL RESOLUTION METHOD OF LENALIDOMIDE

CROSS-REFERENCE TO RELATED APPLICATIONS

This application is a National Stage application of PCT/JP2015/064643, filed May 21, 2015, which claims priority from Japanese application JP 2014-106388, filed May 22, 2014.

BACKGROUND OF THE INVENTION

Field of the Invention

The present invention relates to a method for separating and purifying lenalidomide enantiomers, wherein a racemic mixture of lenalidomide is supplied for chromatography, and an organic solvent selected from the group consisting of aprotic solvents, secondary alcohols and mixtures thereof is used as the mobile phase for optical resolution of each enantiomer of lenalidomide from a mixture (for example, a racemic mixture) of lenalidomide enantiomers.

Related Background Art

Lenalidomide, a derivative of thalidomide, is widely used as an effective immunomodulating drug for different malignant blood diseases such as multiple myeloma. Lenalidomide has been reported to have a superior toxicity profile and more excellent immunomodulatory activity compared to thalidomide (NPL 1). The pharmacokinetic properties of lenalidomide have been elucidated by HPLC methods in reversed-phase mode (NPL 2, NPL 3 and NPL 4), and the final excretion half-life of lenalidomide is conjectured to be about 3 to 4 hours.

In regard to thalidomide and its derivatives and analogs, differences in drug activity have been reported between the R-form and S-form. For example, the sedative action of thalidomide has only been reported with the R-form, (NPL 5), while S-pomalidomide (3-amino-phthalimide-glutarimide) has been reported to significantly inhibit corneal vascularization elicited by bFGF or VEGF, compared to the R-form or racemic form (NPL 6).

Despite such differences in activity between the enantiomers, thalidomide is still administered as a racemic mixture with R-form:S-form=50:50. One of the main reasons for this is its property of very rapid racemization in blood (NPL 7).

The enantiomers of thalidomide have been separated and quantified by repeated extraction using organic solvents, or by chromatographic methods using an enantioselective stationary phase such as modified amylose (NPL 8), cellulose (NPL 7), vancomycin (NPL 9) or methacrylamide (NPL 10), and it has been shown that racemization is very rapid in the blood. Such racemization was first disclosed by G. Blaschke et al., who reported that the racemization half-life of thalidomide in human blood plasma is approximately 10 minutes (NPL 10). This is extremely short considering that the excretion half-life of thalidomide is 8.7 hours (NPL 11).

Because it has such pharmacokinetic properties, it is thought that there is no pharmacological significance in administering a pure enantiomer of thalidomide, and it has been assumed that lenalidomide, which has a basic backbone similar to thalidomide, would also have similar properties. Therefore, the pharmacokinetic and pharmacological properties of the pure enantiomers of lenalidomide have not been thoroughly researched, and absolutely no data has been reported on separation and quantification of pure enantiomers of lenalidomide in biological samples.

CITATION LIST

Non-Patent Literature

[NPL 1] Hideshima T et al., Ther. Clin. Risk. Manag. 2008, 4(1), p. 129-36
[NPL 2] Tohnya™ et al., J. Chromatogr. B Analyt. Technol. Biomed. Life. Sci., 2004, 811(2), p. 135-41
[NPL 3] Chen N et al., Cancer. Chemother. Pharmacol., 2012, 70(5), p. 717-25
[NPL 4] Chen N et al., J Clin Pharmacol., 2007, 47(12), p. 1466-75
[NPL 5] Hoeglund P et al., J. Pharmacokinet. Biopharm., 1998 26(4), p. 363-83
[NPL 6] Lentzsch S et al., Cancer. Res., 2002, 62(8), p. 2300-5
[NPL 7] Eriksson T et al., Chirality., 1995, 7(1), p. 44-52
[NPL 8] Meyring M et al., J. Chromatogr. A. 2000, 876(1-2), p. 157-67
[NPL 9] Murphy-Poulton S F et al., J. Chromatogr. B Analyt. Technol. Biomed. Life. Sci., 2006, 831(1-2), p. 48-56
[NPL 10] Knoche B et al., J. Chromatogr. A., 1994, 666, p. 235-240
[NPL 11] Chen T L et al., Drug. Metab. Dispos., 1989, 17(4), p. 402-5

SUMMARY OF THE INVENTION

It is an object of the present invention to provide a novel method for separating and purifying pure enantiomers of lenalidomide.

The present inventors have found, surprisingly, that enantiomers of lenalidomide reside in the body for a significantly longer time than enantiomers of thalidomide. As mentioned above, it has been assumed that there is no pharmacological significance in administering pure enantiomers of thalidomide because the enantiomers would have a very rapid racemization rate in vivo, but it has been demonstrated that lenalidomide resides in the body as enantiomers for a long period with a non-negligible pharmacological effect, considering its excretion half-life. Evaluation of the pharmacokinetic and pharmacological action of pure enantiomers of lenalidomide therefore potentially has very important significance. Based on this knowledge, the present inventors conducted much diligent research with the aim of solving the problem described above, and as a result have completed this invention upon finding that it is possible to separate and purify pure enantiomers of lenalidomide with controlled decomposition and racemization and containing no artifacts, by using an organic solvent selected from the group consisting of aprotic solvents, secondary alcohols and mixtures thereof as the mobile phase, for optical resolution of an enantiomeric mixture, such as a racemic mixture, of lenalidomide, by chromatography.

Specifically, the invention encompasses the following inventions.

[1] A method for separating and purifying lenalidomide enantiomers, wherein a racemic mixture of lenalidomide is supplied for chromatography, and an organic solvent selected from the group consisting of aprotic solvents, secondary alcohols and mixtures thereof is used as the mobile phase for optical resolution of each enantiomer of lenalidomide from a racemic mixture of lenalidomide.

[2] The method according to [1], wherein the enantiomer of lenalidomide is the S-form.

[3] The method according to [1], wherein the enantiomer of lenalidomide is the R-form.

[4] The method according to any one of [1] to [3], wherein in the optical resolution, the S-form of lenalidomide elutes earlier than the R-form of lenalidomide.

[5] The method according to any one of [1] to [4], wherein the aprotic solvent is ethyl acetate, acetonitrile or a combination thereof.

[6] The method according to any one of [1] to [5], wherein the secondary alcohol is isopropanol.

[7] The method according to any one of [1] to [6], wherein a column is used having a polysaccharide derivative as the stationary phase.

[8] The method according to [7], wherein the column is Chiralpak™ IA or Chiralpak™ IC.

According to the invention, it is possible to efficiently obtain pure enantiomers of lenalidomide. The pure enantiomers of lenalidomide obtained in this manner can be used to elucidate the pharmacokinetic properties or pharmacological properties of the pure enantiomers of lenalidomide in the body, to not only discover possibilities for reducing side-effects or increasing drug effects by administration of the pure enantiomers of lenalidomide, but also to aid in the production of pure enantiomers of lenalidomide. The invention will therefore definitely provide a major contribution to research on the pharmacological drug effects, safety, physical properties and pharmacokinetics of enantiomers of lenalidomide, as well as their application and development in the medical and pharmaceutical industries, including development for their production process.

BRIEF DESCRIPTION OF THE DRAWINGS

FIG. 15(*b*) shows a simple and efficient pretreatment method for lenalidomide analysis method of the invention.

DETAILED DESCRIPTION OF THE INVENTION

Figure 1:
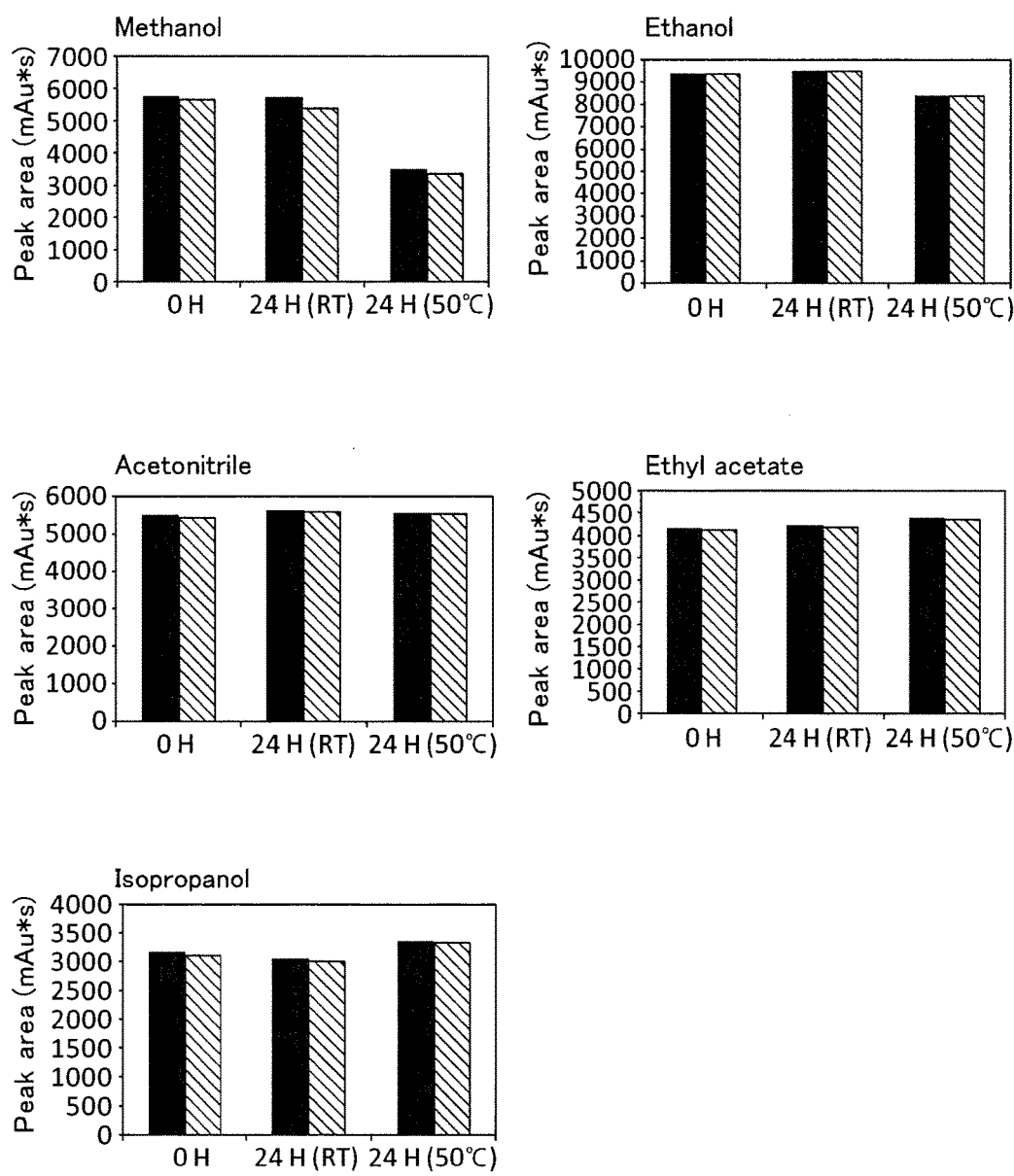
FIG. 1 is a set of graphs showing the stability of lenalidomide stored at room temperature and at 50° C. for 24 hours, in different solvents. The solid black bars represent enantiomer 1, and the diagonally shaded bars represent enantiomer 2.

Lenalidomide (LL) is a derivative of thalidomide (TD) which is known as a therapeutic agent for multiple myeloma, and it is widely used as an effective immunomodulating drug for different malignant blood diseases such as multiple myeloma. It has the chemical structure represented by the following structural formula, having an asymmetric center on a dioxopiperidine ring, similar to thalidomide.

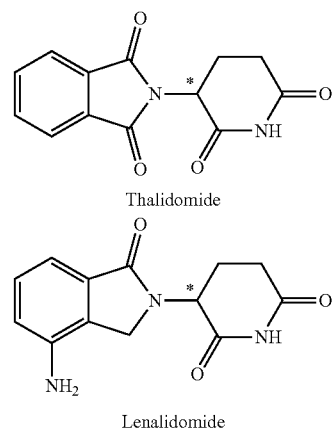

[Chemical Formula 1]

Thalidomide

Lenalidomide

When used in combination with dexamethasone, lenalidomide has a high success rate of 60% for recurrent intractable multiple myeloma, and it is receiving approval throughout the world, having been approved in about 50 countries so far, and has become a blockbuster drug with sales exceeding 400 billion yen. It was approved in 2010 in Japan, but with the condition of compliance with administrative procedures by medical personnel, patients and family, from the viewpoint of ensuring safety, as well as the requirement to investigate the merit of its use in all cases. Lenalidomide has a greater drug effect than thalidomide and fewer side-effects such as sleepiness and numbness, but also, like thalidomide, carries the risk of teratogenicity, and therefore its use is contraindicated for pregnancy. Because lenalidomide is a derivative of thalidomide, it is also expected to racemize rapidly in the blood in the same manner as thalidomide. It is therefore sold as an R-form:S-form=50:50 racemic mixture, and it is currently difficult to obtain pure enantiomers of lenalidomide. Furthermore, since analysis conditions for controlling racemization and accomplishing stable pretreatment and separation have not been established, virtually no data exist regarding the pharmacokinetic properties and racemization rate of pure enantiomers of lenalidomide.

The present inventors have found that it is possible to separate and purify pure enantiomers of lenalidomide with controlled decomposition and racemization, by using an organic solvent selected from the group consisting of aprotic solvents, secondary alcohols and mixtures thereof as the mobile phase, for optical resolution by chromatography. According to one mode of the invention, therefore, there is provided a method for separating and purifying lenalidomide enantiomers, wherein a sample containing an enantiomeric mixture of lenalidomide is supplied for chromatography, and an organic solvent selected from the group consisting of aprotic solvents, secondary alcohols and mixtures thereof is used as the mobile phase for stable optical resolution of each enantiomer of lenalidomide from an enantiomeric mixture of lenalidomide.

In the chromatographic method, a sample containing an enantiomeric mixture in a stationary phase supporting a compound with asymmetric discriminatory power (a chiral discriminator) is supplied together with the organic solvent as the mobile phase, adsorbing each enantiomer and utilizing their difference in retention time for optical resolution of each enantiomer. It is generally carried out using a high-performance liquid chromatography (HPLC) apparatus comprising an optical resolution column.

An aprotic solvent to be used as the mobile phase is not particularly restricted so long as it allows the object of the invention to be achieved, and examples include esters such as acetonitrile and ethyl acetate, ketones such as acetone, ethers such as diethyl ether and diisopropyl ether, and combinations of the foregoing. Preferred are acetonitrile, ethyl acetate and combinations thereof.

A secondary alcohol to be used as the mobile phase is not particularly restricted so long as it allows the object of the invention to be achieved, and examples include isopropanol, 2-butanol, cyclopentanol and cyclohexanol, and combinations of the foregoing. Isopropanol is preferred among these.

The optical resolution column to be used for the method of the invention is not particularly restricted so long as it allows the object of the invention to be achieved, and it may be a normal-phase column or reversed-phase column, or a separation mode column or a multimode column comprising a combination of these. A polysaccharide derivative chiral column will typically be used. A polysaccharide derivative chiral column is a column in which a polysaccharide derivative as the chiral discriminator is immobilized on a support. The polysaccharide derivative supported on the polysaccharide derivative chiral column may be an amylose derivative or cellulose derivative, for example. According to the invention, it is preferred to use Chiralpak™ IA or Chiralpak™ IC.

The optical resolution method of the invention allows pure enantiomers of lenalidomide to be separated and purified from an enantiomeric mixture (such as a racemic mixture) of lenalidomide, without decomposition or racemization.

When pure enantiomers of lenalidomide in a biological sample are to be separated and purified, the macromolecules such as proteins that can lower the low-molecular separation efficiency are generally removed beforehand. Pretreatment of thalidomide has conventionally been carried out by extracting a thalidomide-containing biological sample with a hydrophobic organic solvent (such as an n-hexane/ethyl acetate mixture), either once or several times, drying the obtained organic solvent layer, and then redissolving it in an organic solvent such as dioxane. Lenalidomide, however, has higher polarity than thalidomide and lower solubility in the organic solvent layer, such that the conventional method has had poor efficiency and has been inadequate. In order to solve this problem, the present inventors conducted much diligent research on the effect of pH on racemization of lenalidomide enantiomers, and as a result have found that enantiomers of lenalidomide are highly stable under acidic conditions. According to another mode of the invention, therefore, there is provided a method for pretreatment of a biological sample containing enantiomers of lenalidomide, wherein the biological sample is deproteinized under acidic conditions.

Such acidic conditions are typically pH 5 or lower, preferably in the range of pH 2 to pH 5, and most preferably in the range of pH 4 to pH 5.

The acid to be added to the sample to produce the acidic conditions is not particularly restricted so long as it allows the object of the invention to be achieved, and may be perchloric acid, trichloroacetic acid, trifluoroacetic acid, metaphosphoric acid or hydrochloric acid, or a dicarboxylic acid such as succinic acid or maleic acid.

The biological sample is not particularly restricted so long as it contains lenalidomide, and examples include blood, serum, blood plasma, urine, saliva, breast milk, sweat, spinal fluid, semen, tissue and microsomes.

By supplying a pretreated biological sample containing lenalidomide enantiomers by chromatography, and preferably high-performance liquid chromatography (HPLC), it is possible to conveniently and efficiently separate and quantify enantiomers of lenalidomide in the biological sample.

Moreover, by keeping the fractionated lenalidomide enantiomers in an aqueous buffer under acidic conditions, it is possible to store the lenalidomide enantiomers. Such acidic conditions are typically pH 5 or lower, and preferably in the range of pH 2 to pH 5. The aqueous buffer is not particularly restricted so long as it allows the acidic conditions to be maintained, and examples include citrate buffer, phosphate buffer, acetate buffer, glycine-hydrochloride buffer, MES-HEPES buffer, Tris buffer and borate buffer.

EXAMPLES

Example 1. Stability of Lenalidomide in Different Solvents

A racemic mixture of 0.5 mg/mL lenalidomide in methanol, ethanol, isopropanol, acetonitrile or ethyl acetate, as the sample (product of Selleck Chemicals, US) was incubated at room temperature or at 50° C. for 24 hours, and the following HPLC conditions were employed for quantification of the lenalidomide enantiomers, for evaluation of the stability of lenalidomide in the different solvents.

HPLC Conditions

Apparatus: Nanospace SI-2 Series (Shiseido Corp.)

Column: Chiralpak IA (4.6×250 cm, 5 μm, product of Dicel), RT

Mobile phase: EtOH (100%)

Flow rate: 1.0 mL/min

Injection volume: 5 μL

Detection: UV 230 nm

The peak areas for the enantiomers before and after incubation are shown in FIG. 1 (the initially observed peaks are enantiomer 1, and the next observed peaks are enantiomer 2). Lenalidomide was highly unstable in methanol and ethanol, but no decomposition was observed in acetonitrile and ethyl acetate. Lenalidomide was also stable even in isopropanol. Considering these results, it is thought that decomposition of lenalidomide is accelerated by the weak basicity of the alcohol that attacks the α-carbon atom of the carbonyl group. This does not contradict the results indicating stability of lenalidomide in acetonitrile and ethyl acetate, which are aprotic solvents.

Example 2. Separation of Lenalidomide Enantiomers Using Different Solvents

In order to elucidate the racemization rate of enantiomers of lenalidomide it is very important to separate and quantify the pure enantiomers of lenalidomide. As demonstrated in Example 1, lenalidomide in an alcohol (especially methanol and ethanol) or water (>pH 7) solvent is unstable, and therefore a highly stable aprotic solvent should be used as the mobile phase or sample solvent.

Separation of enantiomers of lenalidomide (LL) and thalidomide (TD) was tested using the different organic solvents listed in Table 1 as the mobile phase, under the following HPLC conditions. The samples used were 0.5 mg/mL LL (Wako Pure Chemical Industries, Ltd.) and TD (Sigma-Aldrich Japan, KK.) dissolved in acetonitrile.

HPLC Conditions

Apparatus: Nanospace SI-2 Series (Shiseido Corp.)

Column: Chiralpak IC (4.6×250 cm, 5 μm, product of Dicel), RT

Mobile phase: Solvent listed in Table 1

Flow rate: 1.0 mL/min

Injection volume: 5 μL

Detection: UV 230 nm or 254 nm

The mobile phase used was an aprotic solvent comprising acetonitrile (ACN), ethyl acetate (EtOAc), tetrahydrofuran (THF) and t-butyl methyl ether (BME). Isopropanol (IPA) is a secondary alcohol, and it was also tested because it has excellent stability, as shown in FIG. 1. The enantiomer separating power was evaluated using the separation factor (RS), defined by the following formula.

$$RS = 2 \times (T_2 - T_1)/(W_1 + W_2)$$

In the formula, numeral 1 and numeral 2 refer to enantiomer 1 and enantiomer 2, respectively (peak 1 eluting before peak 2), T represents the retention time, and W represents the peak width. Table 1 shows the separation of LL enantiomers when using different solvents as the mobile phase.

[Table 1]

TABLE 1

Enantiomer separation using Chiralpak IC with different inert mobile phases

| Method No. | Mobile phase composition (%) | | | | | Separation | |
|---|---|---|---|---|---|---|---|
| | ACN | EtOAc | THF | IPA | tBu—O—Me | LL | TD |
| 01 | 100 | | | | | 7.26 | 2.51 |
| 02 | | 100 | | | | 12.51 | 0.59 |
| 03 | | | 100 | | | 2.93 | NS |
| 04 | 75 | 25 | | | | 6.33 | 1.08 |
| 05 | 75 | | 25 | | | 2.05 | NS |
| 06 | 75 | | | 25 | | 4.78 | NS |
| 07 | 50 | 50 | | | | 6.40 | NS |
| 08 | 50 | | 50 | | | NS | NS |
| 09 | 50 | | | 50 | | 4.51 | NS |
| 10 | | 50 | 50 | | | 4.90 | NS |
| 11 | | 50 | | 50 | | NS | NS |
| 12 | | 50 | 25 | 25 | | 4.04 | NS |
| 13 | | | 50 | 50 | | 1.53 | NS |
| 14 | 50 | 25 | 25 | | | 2.45 | 1.43 |
| 15 | 25 | 75 | | | | 7.62 | 1.84 |
| 16 | | 75 | 25 | | | 8.24 | 1.35 |
| 17 | | 75 | | 25 | | 10.11 | NS |
| 18 | | | | | 100 | NS | NS |

NS: No separation

Figure 2:
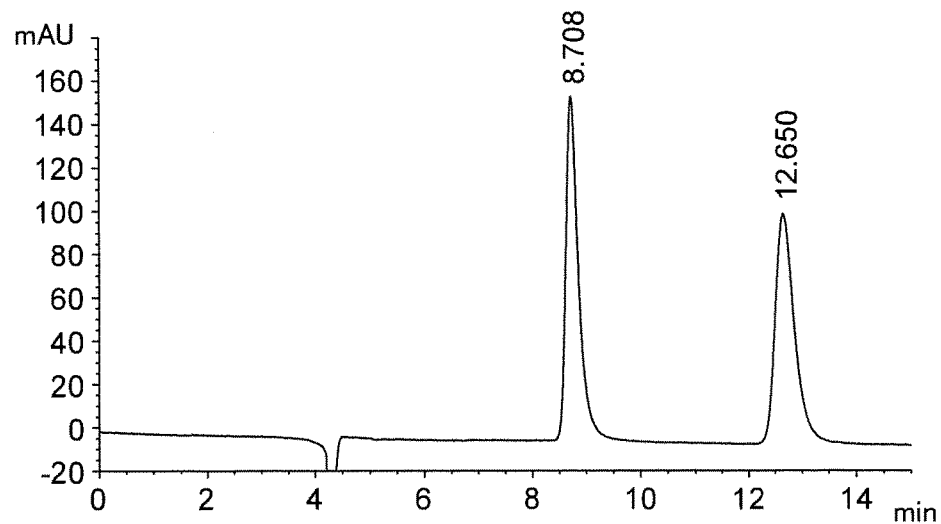
FIG. 2 shows separation of lenalidomide enantiomers using Chiralpak IC (4.6 mm i.d.×250 mm) as the optical resolution column, with ethyl acetate as the mobile phase.

Among these mobile phases, the most effective ones for separation of LL enantiomers was ethyl acetate, the highest separation being obtained when using ethyl acetate as the mobile phase (Table 1, No. 02) (RS=12.51). FIG. 2 shows that LL enantiomers were satisfactorily separated when using ethyl acetate as the mobile phase. Moreover, using a mobile phase with a fixed amount of ethyl acetate mixed exhibited more excellent separation than when no ethyl acetate was present or the amount was very low (for example, No. 3, 10, 11 and 17). These results demonstrated that ethyl acetate is a highly superior solvent as the mobile phase in chromatography for LL enantiomer separation.

Acetonitrile also exhibited satisfactory separation (Table 1, No. 01, RS=7.26). Since acetonitrile also exhibits excellent stability as shown in FIG. 1, it can serve as a satisfactory solvent for the mobile phase in chromatography for separation of LL enantiomers.

For TD, on the other hand, sufficient separation was not observed when using any solvent as the mobile phase.

Example 3. Preparation of Pure Enantiomers of Lenalidomide

A method for preparing pure enantiomers of lenalidomide was established, based on the results for stability and enantiomer separation of lenalidomide. Specifically, pure enantiomers of lenalidomide were prepared according to the following scheme and HPLC conditions.

TABLE 2

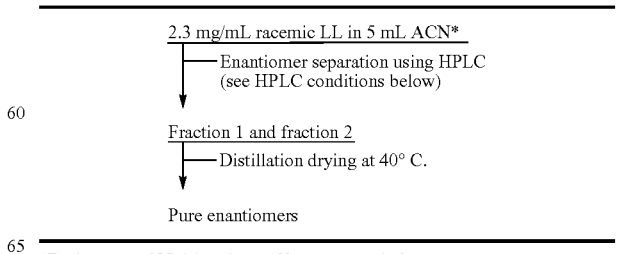

*Total amount of LL injected was 180 mg as racemic form.

Figure 3:
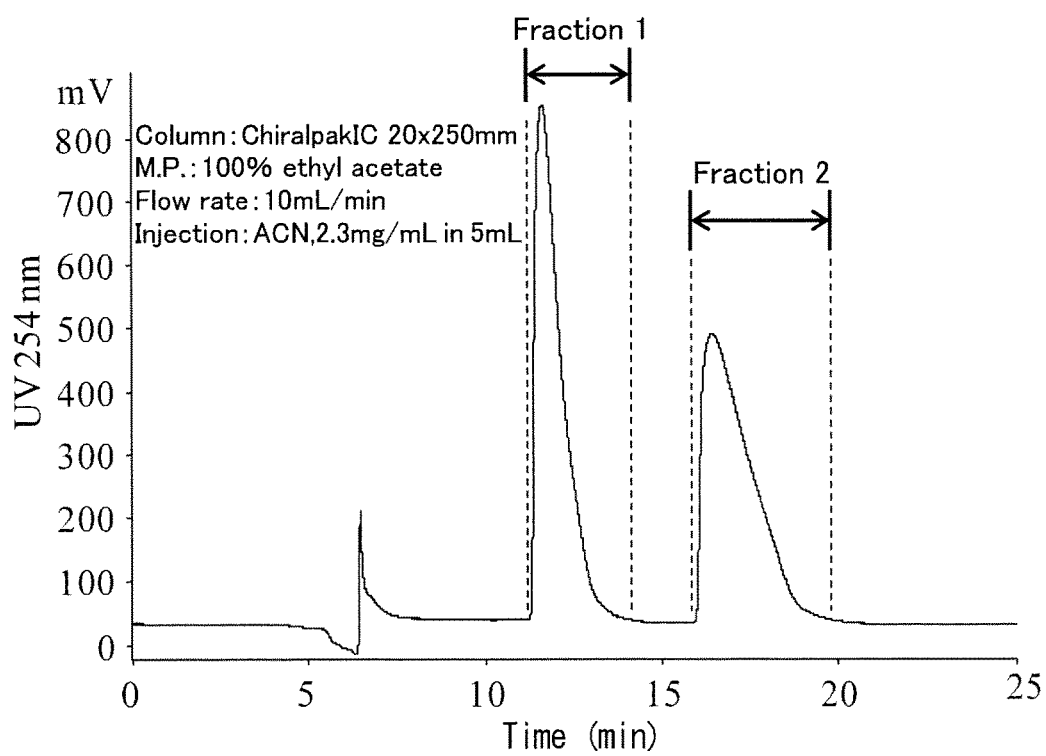
FIG. 3 shows purification of lenalidomide enantiomers with Chiralpak IC (20 mm i.d.×250 mm) as the optical resolution column, and with ethyl acetate as the mobile phase. The enantiomer eluted in fraction 1 was designated as LL1, and the enantiomer eluted in fraction 2 was designated as LL2.
Figure 4:
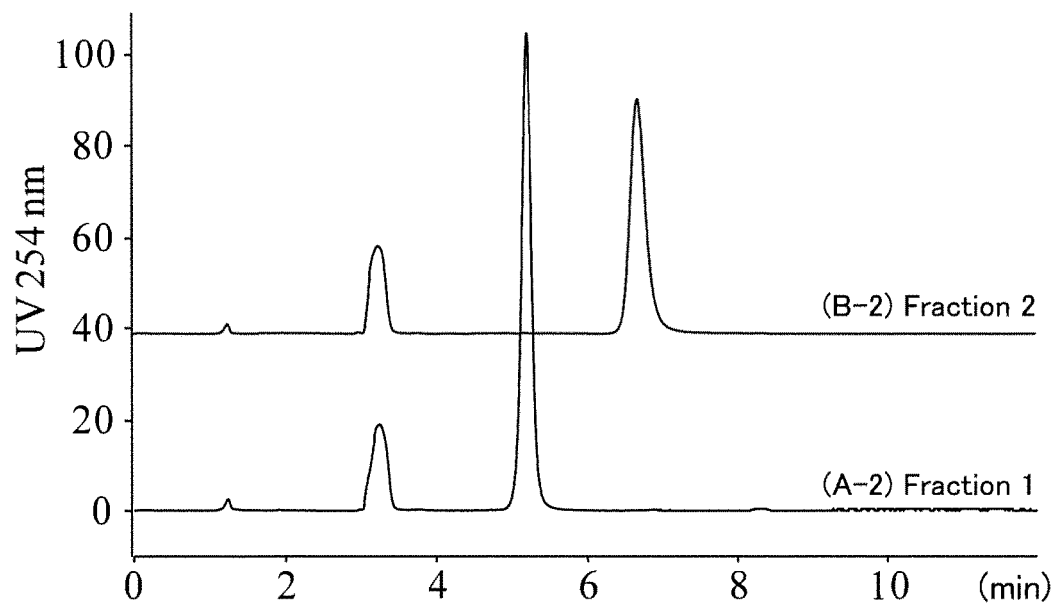
FIG. 4 is a set of chromatograms of purified (fractionated) enantiomers in fraction 1 (A-1) and fraction 2 (B-1). Chiralpak IA was used for the analysis.
Figure 4:
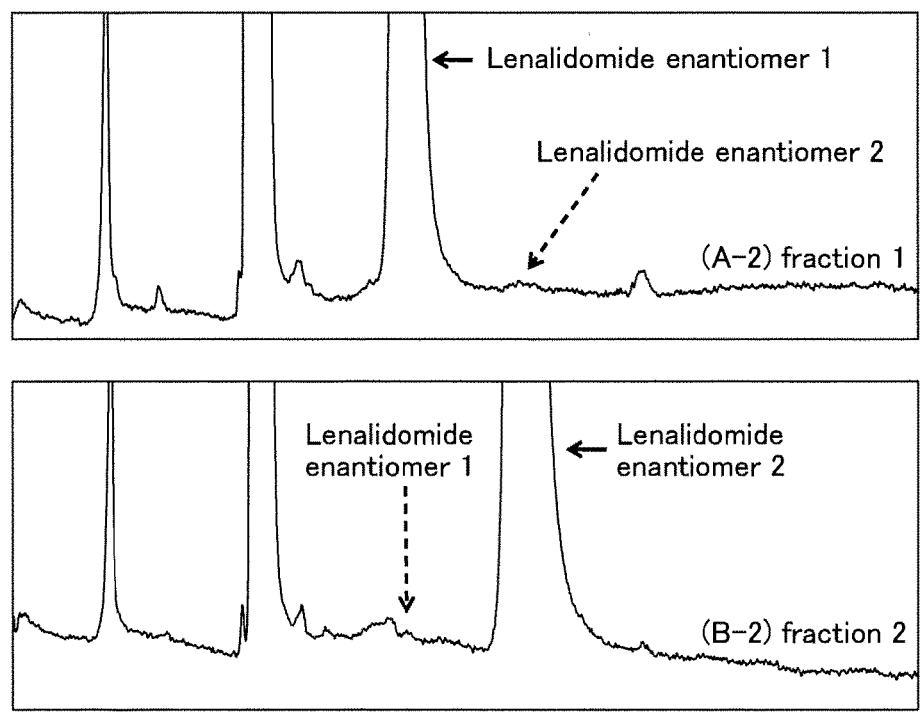

HPLC Conditions
Apparatus: HPD PUMP and LAMBDA1010 (Bischoff Co.)
Column: Chiralpak IC (2.0 mm i.d.×250 cm, 5 µm, product of Dicel), RT
Mobile phase: Ethyl acetate
Flow rate: 10 mL/min
Injection volume: 2.3 µL/mL LL racemic mixture in 5000 µL of acetonitrile
Detection: UV 254 nm As shown in FIG. 3, the LL enantiomers were completely separated. After separating off the fractions and drying them, over 80 mg of the pure enantiomers was obtained from 180 mg of the racemic mixture. The fractions were dissolved in acetonitrile (1 or 0.1 mg/mL) and stored at −25° C. Based on the integral peak areas in the chromatograms shown in FIG. 4 (A-2, B-2), fraction 1 and fraction 2 recovered as lenalidomide enantiomer 1 (LL1) and lenalidomide enantiomer 2 (LL2) exhibited sufficient enantiomer purities of 99.02% and 99.96%, respectively.

Figure 5:
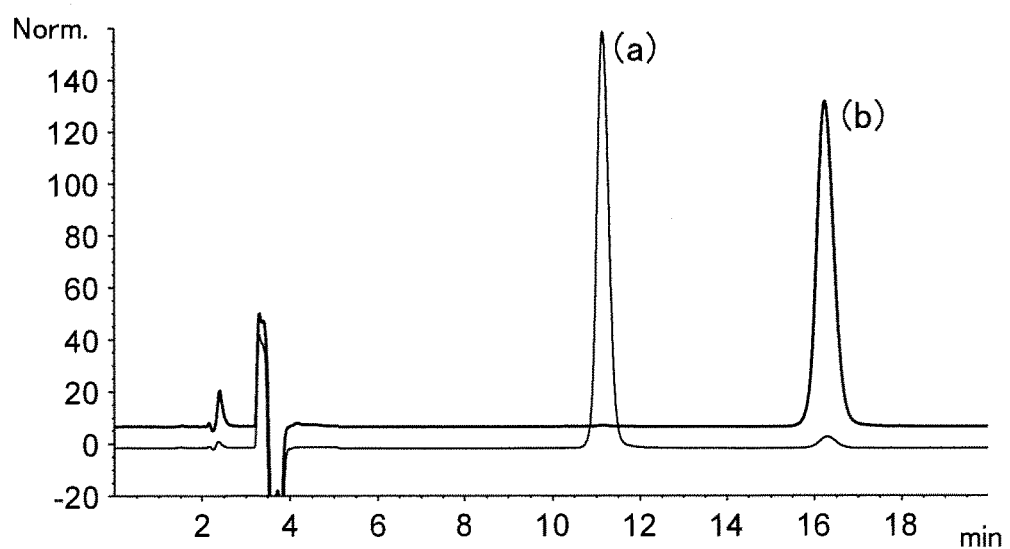
FIG. 5 is a chromatogram showing S-thalidomide (a) and R-thalidomide (b).

Example 4. Inference of Absolute Configurations of LL1 and LL2 from Elution Order The absolute configurations of LL1 and LL2 can be reasonably inferred by comparing the order of elution of LL1 and LL2 with commercially available R-thalidomide and S-thalidomide (Sigma-Aldrich Japan, KK.). The order of elution was confirmed with the following HPLC conditions.
HPLC Conditions
Apparatus: Nanospace SI-2 Series (Shiseido Corp.)
Column: Chiralpak IA (4.6 mm i.d.×250 cm, 5 µm, product of Dicel), RT
Mobile phase: 0.1% Formic acid in EtOH/H$_2$O (95/5, v/v)
Flow rate: 0.75 mL/min
Injection volume: 5 µL of 0.1 mg/mL (S)-TD, (R)-TD
Detection: UV 230 nm As clearly seen from FIG. 5, S-thalidomide eluted earlier than R-thalidomide. Considering that LL1 elutes earlier than LL2 under the same HPLC conditions, presumably the absolute configuration of LL1 corresponds to the S-enantiomer while the absolute configuration of LL2 corresponds to the R-enantiomer (hereunder, LL1 and LL2 will be defined as S*-LL and R*-LL).

Example 5. Dependence of Racemization Half-Life on pH

In order to elucidate the racemization half-life of lenalidomide and its pH dependence, an experiment was conducted with the following scheme and HPLC conditions.

TABLE 3

1 mg/mL (S*)-LL in 30 µL ACN
— Drying with N$_2$ stream
← 50 mM aqueous buffer (pH 4-9, see table below)
— Incubation for 0, 1, 3, 5, 8, 12, 16 and 14 hours at room temperature (controlled to 25° C.)

5 µL to HPLC

TABLE 4

| pH | Measured pH | Buffer |
|---|---|---|
| 4 | 3.98 | 0.05M Na-citrate buffer |
| 5 | 5.00 | |
| 6 | 6.02 | |
| 7(a) | 6.97 | 0.05M NH$_4$-acetate buffer |
| 7(b) | 7.04 | 0.05M Na-phosphate buffer |
| 8 | 7.96 | 0.05M Tris-HCl buffer |
| 9 | 9.03 | |

Figure 6:
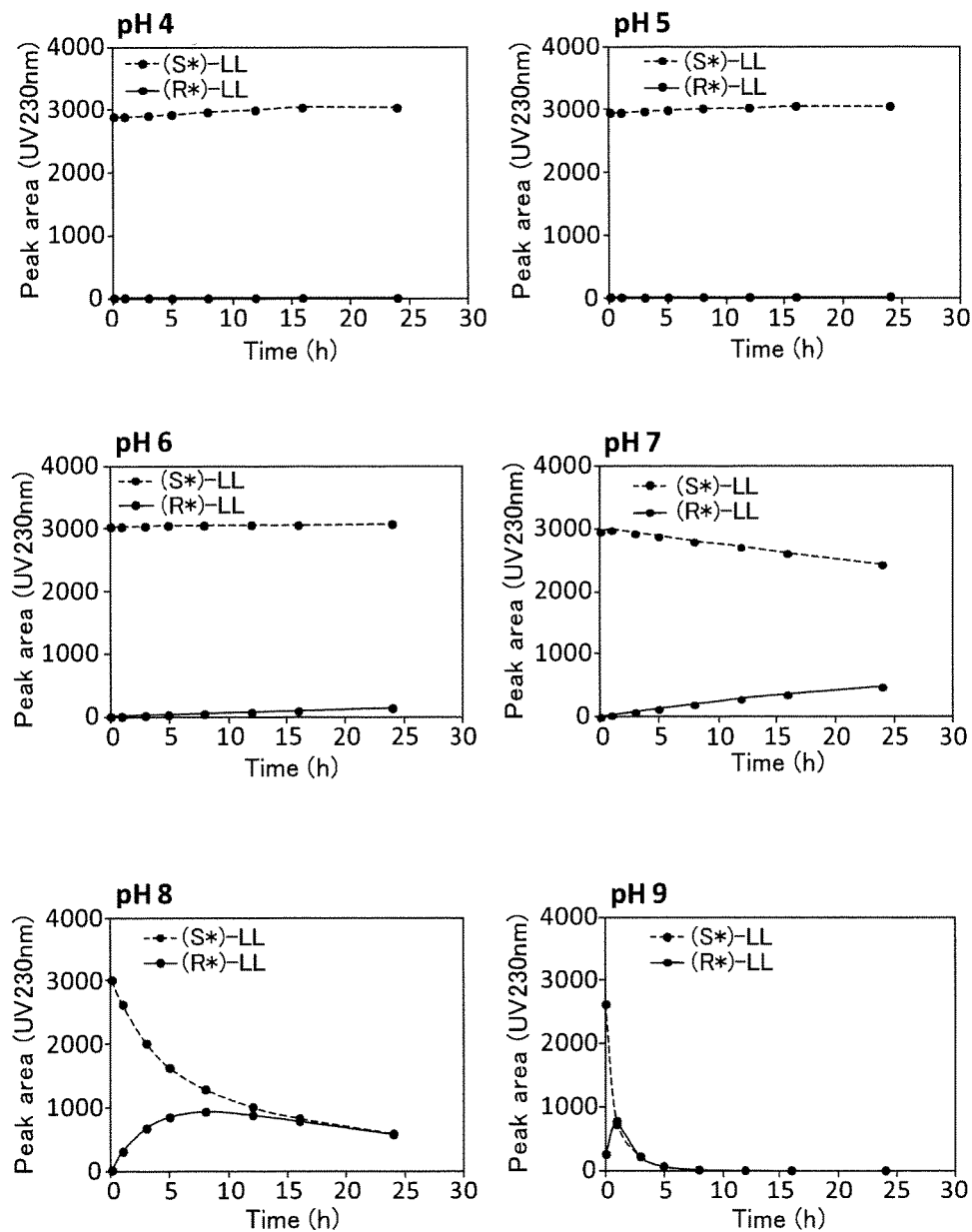
FIG. 6 shows time-dependent changes in the peak area of (S*)-LL and (R*)-LL after adding aqueous buffer at room temperature.

HPLC Conditions
Apparatus: Nanospace SI-2 Series (Shiseido Corp.)
Column: Chiralpak IA (4.6 mm i.d.×250 cm, 5 µm, product of Dicel), RT
Mobile phase: 0.1% Formic acid in EtOH/H$_2$O (95/5, v/v)
Flow rate: 0.75 mL/min
Injection: 5 µL
Detection: UV 230 nm The variation in (S*)-LL at different pH is shown in FIG. 6. A small amount of (R*)-LL was produced with incubation at pH 6, while racemization was significantly accelerated at pH 7 and higher. Since the peak areas of (S*)- and (R*)-LL were reduced at pH 9 and 8, it was concluded that racemization and decomposition of LL takes place under these pH conditions.

Figure 7:
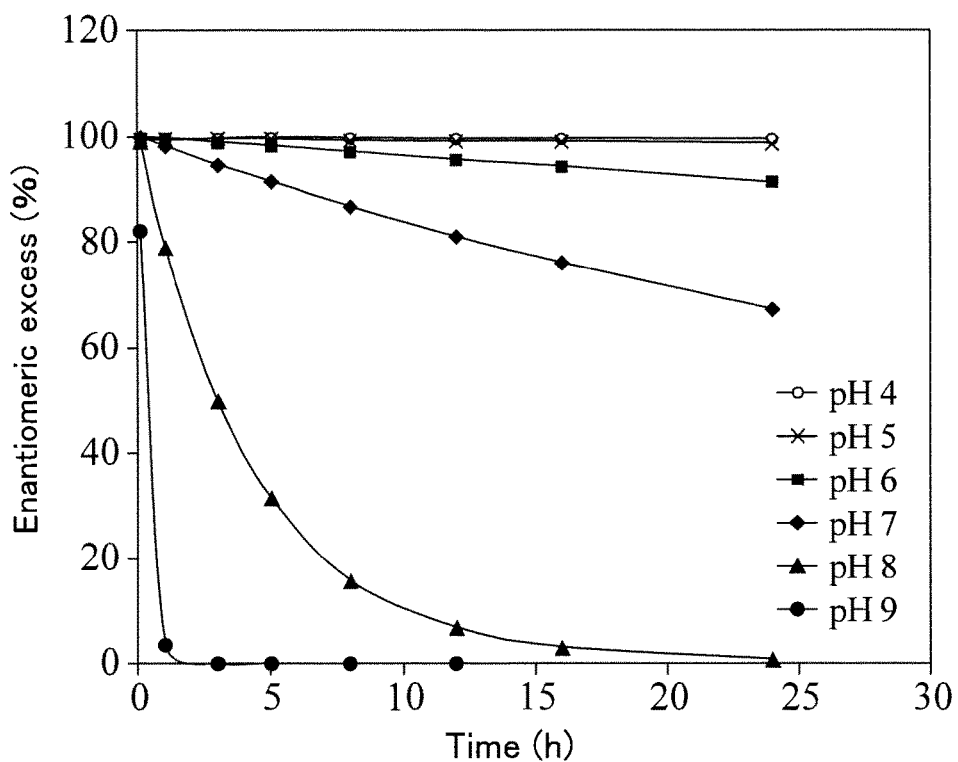
FIG. 7 shows time-dependent changes in enantiomer excess in aqueous buffers (pH 4 to 9) at room temperature.
Figure 8:
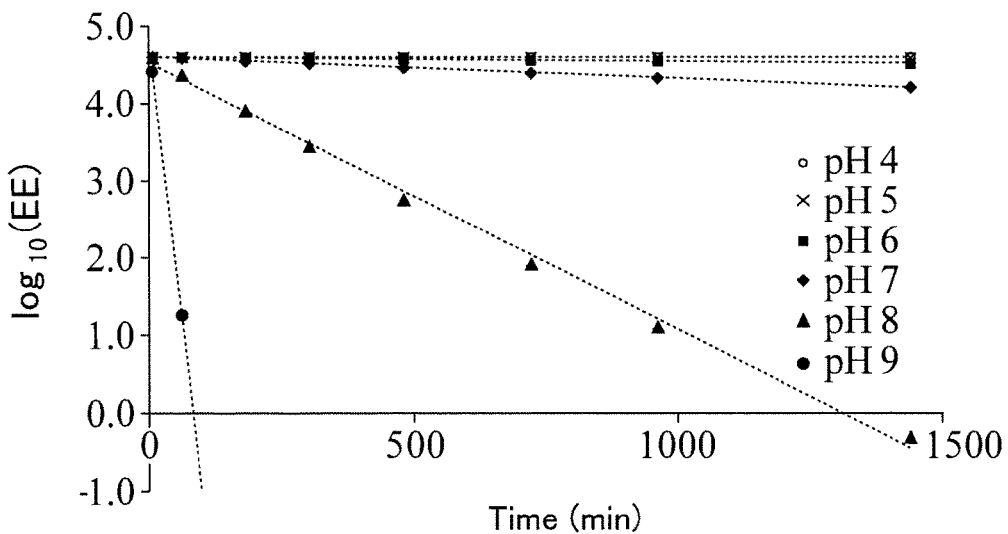
FIG. 8 is a plot of $\log_{10}$ (Enantiomer Excess) with respect to time, at room temperature.

The enantiomeric excess rate (EE, [(S−R)/(S+R)×100], %) at each point is plotted in FIG. 7, and the log$_{10}$ (EE) vs. time plot is shown in FIG. 8. As reported for thalidomide, since racemization is thought to be a pseudo-first-order reaction, FIG. 8 shows an approximately ideal straight line.

This linearity was used to calculate the time for EE=50 based on a straight line approximation (y=ax+b), to determine the racemization half-life. The stability of the pure enantiomer is very highly dependent on pH, the half-life being 10 times longer for every pH reduction of 1, and estimation of the half-life was no longer possible at pH 4. At pH 9, on the other hand, sudden racemization and decomposition were observed. These results clearly indicate that enantiomers of lenalidomide are stable under acidic conditions (<pH 4).

Example 6. Establishing Biological Sample Pretreatment Method

Numerous reports already exist of measuring thalidomide or lenalidomide in blood (serum and blood plasma) or urine using HPLC. Measurement of enantiomers of TD in biological samples has been reported, and the racemization half-life has been determined both in vivo and in vitro (Eriksson T et al., Chirality., 1995, 7(1), p. 44-52 and Knoche B et al., J. Chromatogr. A., 1994, 666, p. 235-240). These measurements are all based on liquid-liquid extraction methods. The conventional method is shown as scheme (a). Measurement is possible by this method because an aprotic solvent is essentially inert to racemization or decomposition. However, since the solubility of thalidomide or lenalidomide is not high in hydrophobic organic solvents, it is necessary to use a large amount of solvent and carry out repeated extraction.

A very simple and efficient pretreatment method for lenalidomide was therefore established, based on the knowledge of enantiomer stability under acidic conditions demonstrated in Example 5. The analysis method of the invention is shown as scheme (b). The acid used to suspend the reaction while simultaneously precipitating and removing the protein was HClO$_4$.

TABLE 5

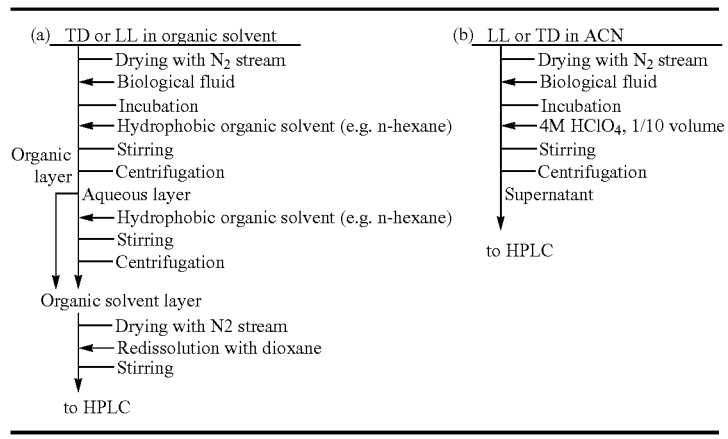

Figure 9:
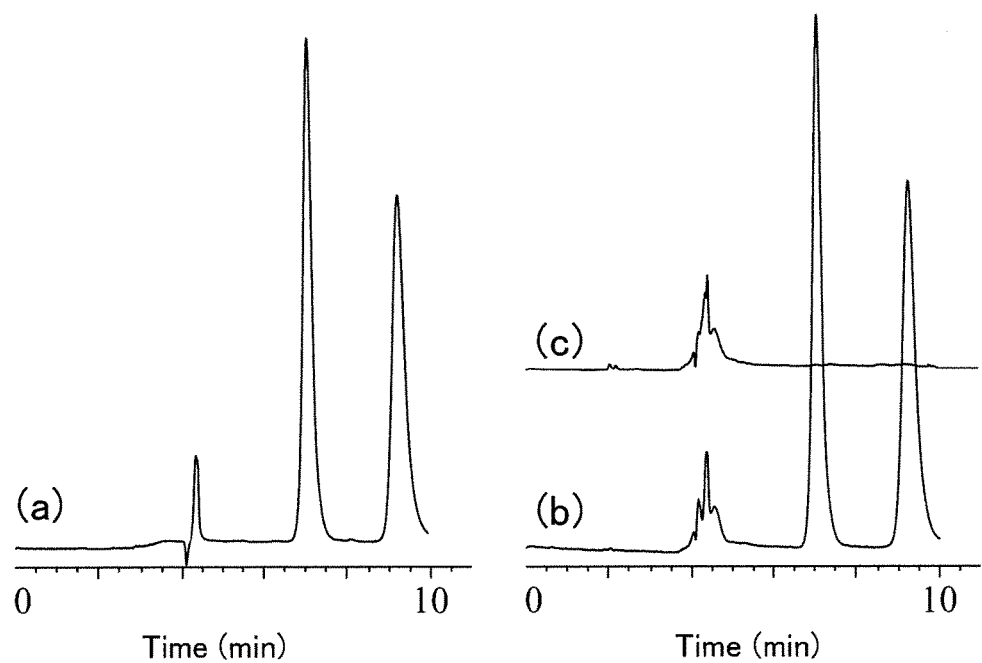
FIG. 9 is a pair of chromatograms of (a) LL enantiomer in water (control) and (b) LL enantiomer in human serum. Sample: (a) 0.1 mg/ml racemic LL in water, (b) 0.1 mg/ml racemic LL in human serum, (c) LL-free human serum. $HclO_4$ was added immediately after dissolving the LL in serum or water. HPLC conditions: Column: Chiralpak IA (4.6 mm i.d.×250 cm)+Security guard C8 (3.0 mm i.d.×4 mm), flow rate: 0.75 mL/min, injection rate: 2 µL.

FIG. 9 shows chromatograms obtained using the method of scheme (b). As shown in FIG. 9(b), lenalidomide enantiomers in serum can be satisfactorily separated and quantified without being affected by contaminating components such as proteins, and therefore the method can be applied to biological samples as well.

Example 7. Racemization of Lenalidomide Under Physiological Conditions

The obtained pure enantiomers were used to evaluate the racemization rate of lenalidomide under biological buffer conditions (pH 7.4, 37° C.) and in human serum (37° C.), by the following scheme.

TABLE 6

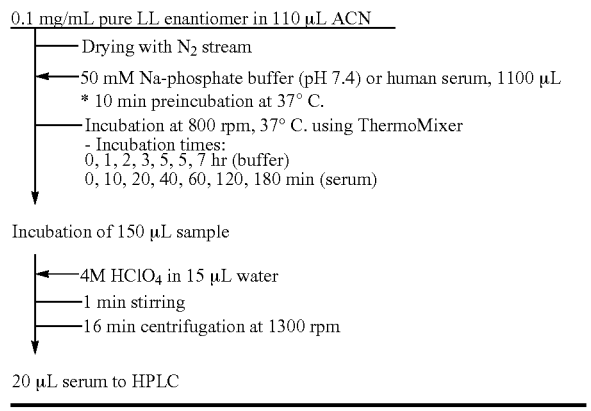

Figure 10:
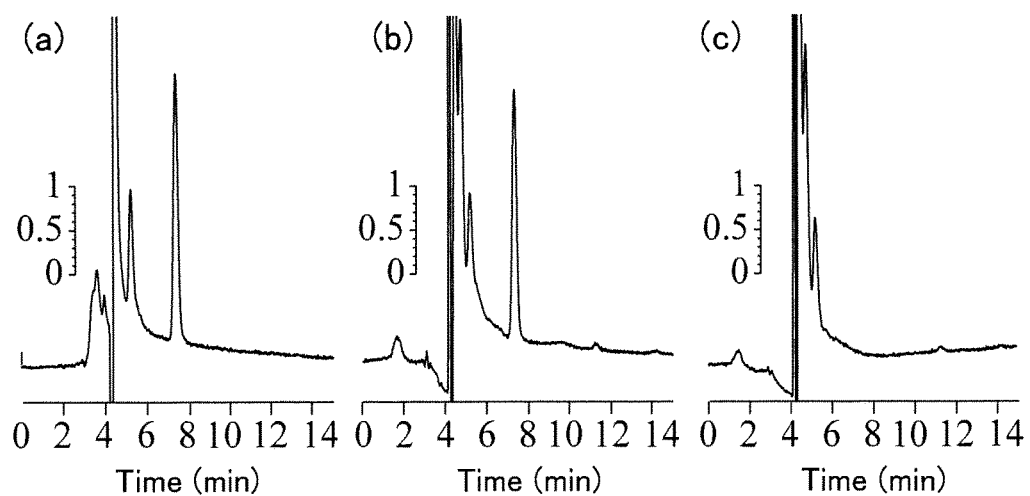
FIG. 10 is a set of chromatograms of (a) 0.01 mg/mL LL in Na-phosphorate buffer (pH 7.4), (b) 0.01 mg/mL LL in serum, and (c) LL-free blank serum.

HPLC Conditions
Apparatus: Nanospace SI-2 Series (Shiseido Corp.)
Column: Chiralpak IA (4.6 mm i.d.×250 cm, 5 μm)+Security guard C8 (3.0 mm i.d.×4 mm)
Temperature: 40° C.
Mobile phase: 0.1% Formic acid in EtOH/$H_2O$ (95/5, v/v)
Flow rate: 0.75 mL/min
Injection: 20 μL
Detection: UV 230 nm As clearly seen from the chromatogram for (S*)-LL shown in FIG. 10 [0.01 mg/mL (a) in buffer, (b) in serum], the method of the invention has sufficient retention and separation and detection sensitivity (signal-to-noise ratio). The blank sample (c) derived from serum alone without LL contained no contaminants that inhibit measurement of LL in the method of the invention. The peak area for (S*)-LL in FIG. 18(b) was 91% of FIG. 18(a). This indicates an adequate recovery rate for pretreatment of lenalidomide in serum.

Figure 11:
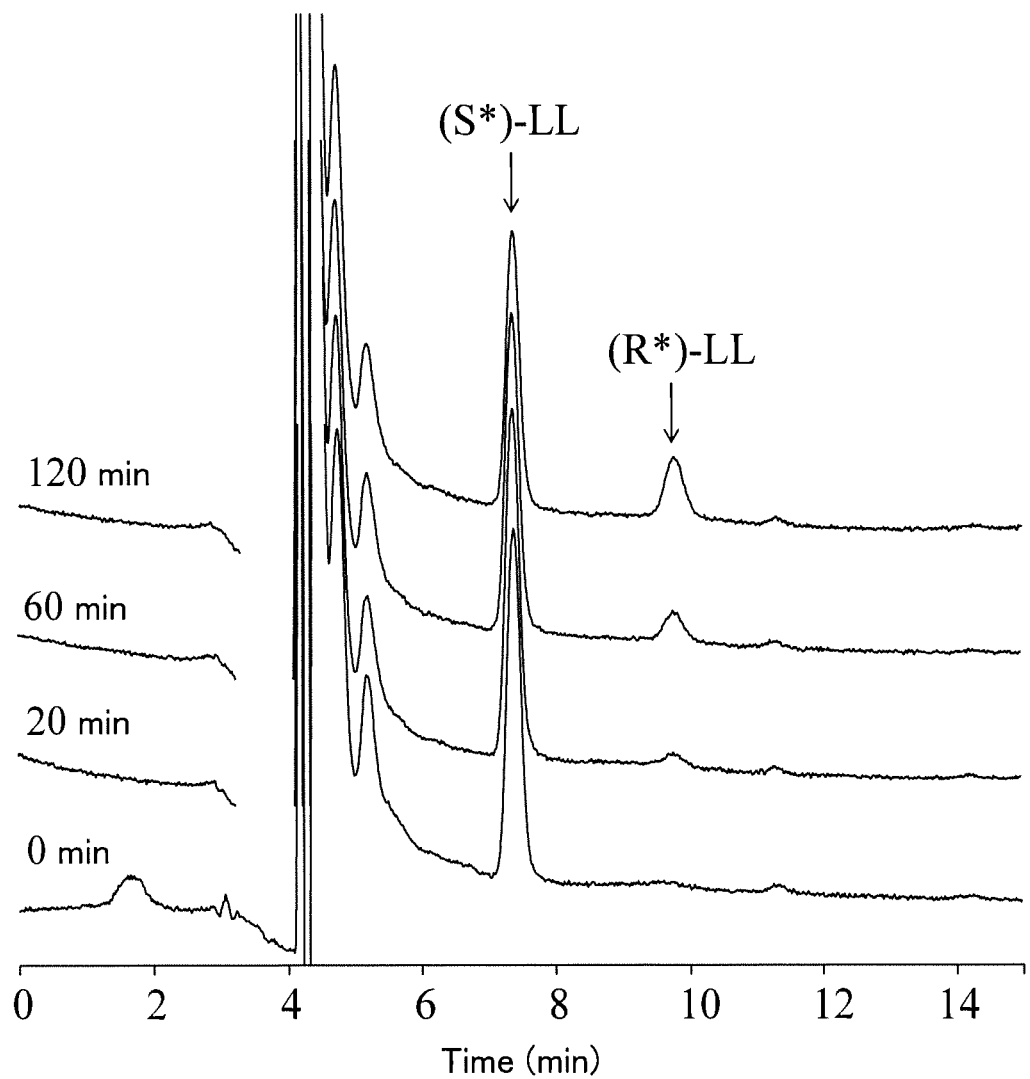
FIG. 11 is a chromatogram for human serum at 37° C., after adding 10 µg/mL of (S*)-LL.

FIG. 11 shows continuous change in the chromatogram for incubation of S*-LL. The LL enantiomers were separated and quantified to a sufficient level for detection of racemization product, without being inhibited by other substances in the sample.

The racemization half-life was calculated by the same method described in Example 5. The racemization half-life in aqueous buffer was estimated from this, as follows: (S*)-LL, (R*)-LL, (S)-TD and (R)-TD=272±1.3, 267±1.1, 266±10 and 295±24 (min), respectively. These results demonstrated that at pH 7.4, LL enantiomers have a similar half-life as TD in aqueous buffer.

Figure 12:
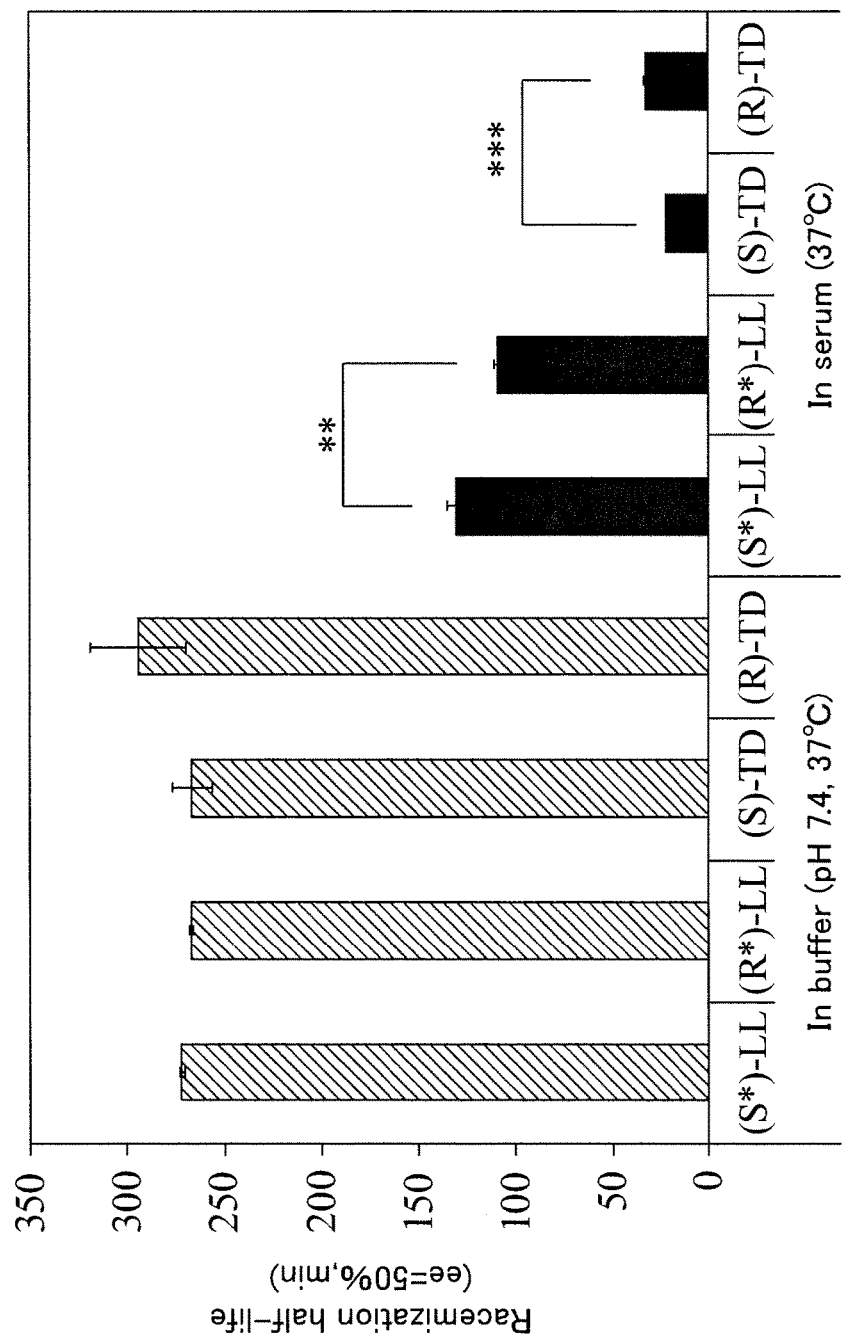
FIG. 12 shows the racemization half-lives of LL and TD enantiomers in Na-phosphorate buffer (pH 7.4, diagonal-shaded bars) and human serum (solid black bars). The bar graphs represent the average values for 3 tests, and the error bars represent SD. The significant differences were $p<0.01$ and *$p<0.001$.
Figure 13:
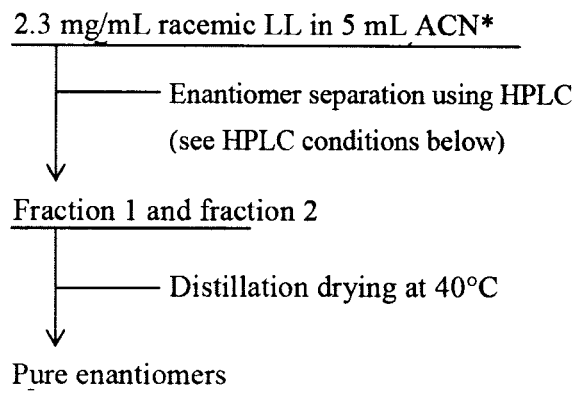
FIG. 13 shows a scheme for preparing pure enantiomers of lenalidomide.
Figure 14:
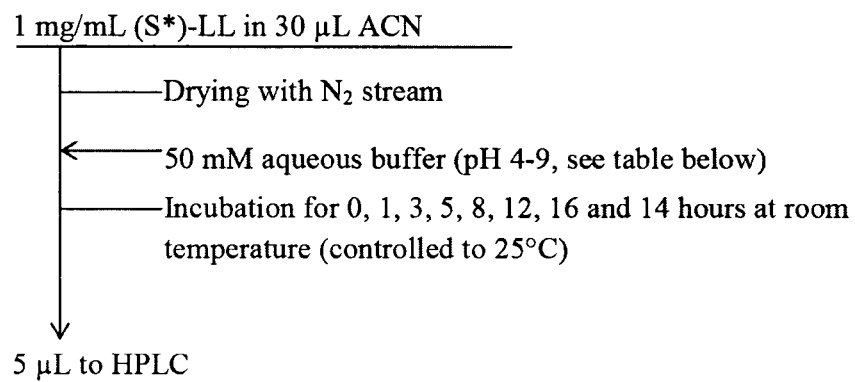
FIG. 14 shows a scheme of an experiment to elucidate the racemization half-life of lenalidomide and its pH dependence.
Figure 15A:
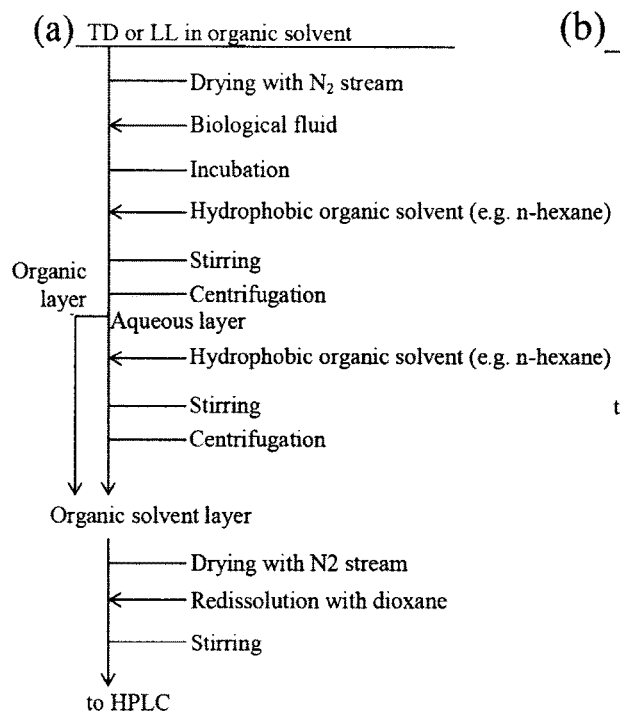
FIG. 15(*a*) shows the conventional method of measuring thalidomide or lenalidomide in blood (serum and blood plasma) or urine using HPLC.
Figure 15B:
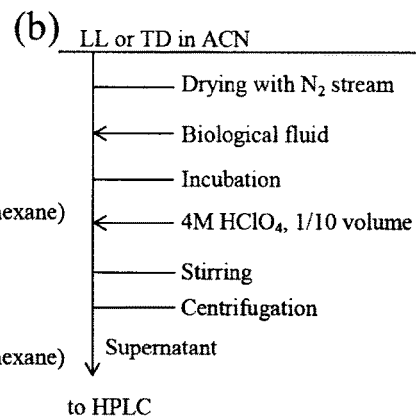
Figure 16:
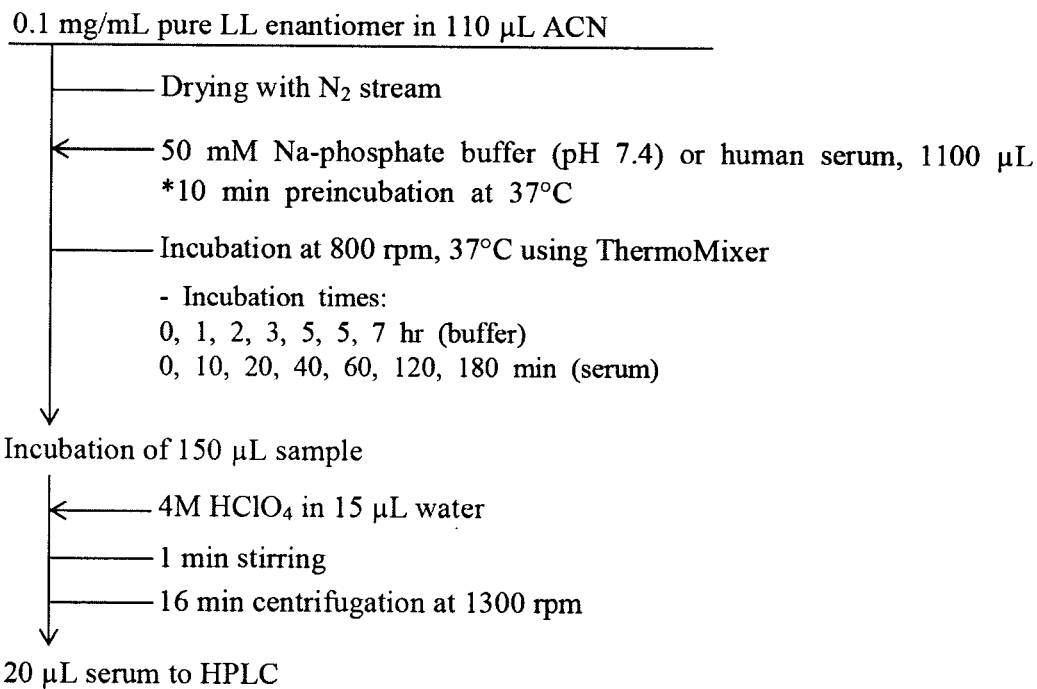
FIG. 16 shows a scheme showing the obtained pure enantiomers used to evaluate the racemization rate of lenalidomide under biological buffer conditions (pH 7.4, 37° C.) and in human serum (37° C.)

The half-life in human serum was calculated in the same manner: (S*)-LL, (R*)-LL, (S)-TD and (R)-TD=131±4.9, 109±2.0, 21.8±1.0 and 32.9±25 (min), respectively. The results are shown in FIG. 12. Thalidomide in human serum has a half-life of only 8.2% (S-form) and 11.1% (R-form) compared to buffer, indicating that racemization of thalidomide is extremely accelerated in serum. It is believed that the accelerated racemization for these enantiomers is due to the biomolecules including proteins such as human albumin in serum.

For LL in serum, the results showed that (S*)-LL has a racemization half-life of 6 times longer than (S)-TD, while (R*)-LL has a racemization half-life of 3 times longer than (R)-TD. These results clearly indicate that the LL enantiomers, and especially (S*)-LL, are much more stable compared to thalidomide. In contrast to TD, (S*)-LL was more stable than (R*)-LL. This difference in the half-lives of the S- and R-enantiomers should also be noted.

What is claimed is:

1. A method for separating and purifying lenalidomide enantiomers, wherein an enantiomeric mixture of lenalidomide is supplied to chromatography, and an organic solvent selected from the group consisting of aprotic solvents, secondary alcohols and mixtures thereof is used as the mobile phase for optical resolution of each enantiomer of lenalidomide from a racemic mixture of lenalidomide, wherein the aprotic solvent is ethyl acetate, acetonitrile, or a combination thereof.

2. The method according to claim 1, wherein the enantiomer of lenalidomide is the S-form.

3. The method according to claim 1, wherein the enantiomer of lenalidomide is the R-form.

4. The method according to claim 1, wherein in the optical resolution, the S-form of lenalidomide elutes earlier than the R-form of lenalidomide.

5. The method according to claim 1, wherein the secondary alcohol is isopropanol.

6. The method according to claim 1, wherein a column is used having a polysaccharide derivative as the stationary phase.

7. The method according to claim 6, wherein the column is Chiralpak™ IA or Chiralpak™ IC.

* * * * *